United States Patent
Wösle

(10) Patent No.: US 11,607,564 B2
(45) Date of Patent: Mar. 21, 2023

(54) METHOD FOR EPID-BASED VERIFICATION, CORRECTION AND MINIMIZATION OF THE ISOCENTER OF A RADIOTHERAPY DEVICE

(71) Applicant: STÄDTISCHES KLINIKUM DESSAU, Dessau-Roßlau (DE)

(72) Inventor: Markus Wösle, Dessau-Roßlau (DE)

(73) Assignee: STÄDTISCHES KLINIKUM DESSAU, Dessau-Roßlau (DE)

( * ) Notice: Subject to any disclaimer, the term of this patent is extended or adjusted under 35 U.S.C. 154(b) by 309 days.

(21) Appl. No.: 16/651,254

(22) PCT Filed: Sep. 27, 2018

(86) PCT No.: PCT/DE2018/000275
§ 371 (c)(1),
(2) Date: Mar. 26, 2020

(87) PCT Pub. No.: WO2019/063035
PCT Pub. Date: Apr. 4, 2019

(65) Prior Publication Data
US 2020/0289850 A1    Sep. 17, 2020

(30) Foreign Application Priority Data
Sep. 27, 2017   (DE) .................... 10 2017 009 040.8

(51) Int. Cl.
*A61N 5/10*    (2006.01)
(52) U.S. Cl.
CPC ......... *A61N 5/1049* (2013.01); *A61N 5/1042* (2013.01); *A61N 5/1075* (2013.01);
(Continued)

(58) Field of Classification Search
CPC .. A61N 5/1049; A61N 5/1042; A61N 5/1075; A61N 5/1081; A61N 2005/1054; A61N 2005/1076; A61N 5/1048
See application file for complete search history.

(56) References Cited

U.S. PATENT DOCUMENTS 6,240,162 B1    5/2001    Hernandez-Guerra et al.
8,130,905 B1    3/2012    Nelms
(Continued)

FOREIGN PATENT DOCUMENTS

| CN | 102083498 A | 6/2011 |
| CN | 102921115 A | 2/2013 |

(Continued)

OTHER PUBLICATIONS

Arjomandy, B., & Altschuler, M. D. (2000). A quality assurance device for the accuracy of the isocentres of teletherapy and simulation machines. Physics in Medicine and Biology, 45(8), 2207-2217. https://doi.org/10.1088/0031-9155/45/8/310 (Year: 2000).*

(Continued)

*Primary Examiner* — Thaddeus B Cox
*Assistant Examiner* — Marc D. Honrath
(74) *Attorney, Agent, or Firm* — Smartpat PLC

(57) ABSTRACT

A method for EPID-based verification, correction and minimization of the isocenter of a radiotherapy device includes the following: Positioning a measurement body; applying an irradiation field; capturing a common dose image of the measurement body; creating a dose profile on the basis of the captured dose image; determining an inflection point in a plot of the dose profile; linking positions of the inflection points to bodily limits of the measurement body; determining position of a center point of the measurement body relative to an EPID-center; determining a differential vector from a deviation in position of the center point of the (Continued)

measurement body from the EPID-center and from a deviation in position of the field center point of the irradiation field from the EPID-center; and correcting the current radiological isocenter.

14 Claims, 9 Drawing Sheets

(52) U.S. Cl.
CPC .... *A61N 5/1081* (2013.01); *A61N 2005/1054* (2013.01); *A61N 2005/1076* (2013.01)

(56) References Cited

U.S. PATENT DOCUMENTS

| | | | |
|---|---|---|---|
| 9,192,784 B1* | 11/2015 | Ritt | G06T 11/005 |
| 2003/0204336 A1 | 10/2003 | Ritt | |
| 2005/0151071 A1 | 7/2005 | Nilsson | |
| 2007/0071169 A1 | 3/2007 | Yeo et al. | |
| 2012/0232324 A1 | 9/2012 | Brusasco et al. | |
| 2014/0330108 A1 | 11/2014 | Dempsey | |
| 2015/0036806 A1 | 2/2015 | Wong | |
| 2015/0360056 A1 | 12/2015 | Xing et al. | |
| 2016/0023019 A1* | 1/2016 | Filiberti | A61N 5/1069 600/1 |
| 2016/0136459 A1 | 5/2016 | Verhaegen et al. | |
| 2016/0361570 A1 | 12/2016 | Sayeed | |

FOREIGN PATENT DOCUMENTS

| | | |
|---|---|---|
| CN | 105031833 A | 11/2015 |
| CN | 105204056 A | 12/2015 |
| CN | 106237545 A | 12/2016 |
| CN | 106902477 A | 6/2017 |
| CN | 107126634 A | 9/2017 |
| EP | 3106205 A1 | 12/2016 |
| WO | 0224277 A1 | 3/2002 |

OTHER PUBLICATIONS

Rowshanfarzad, P., Sabet, M., O'Connor, D. J., & Greer, P. B. (2011). Isocenter verification for LINAC-based Stereotactic Radiation therapy: Review of principles and techniques. Journal of Applied Clinical Medical Physics, 12(4), 185-195. https://doi.org/10.1120/jacmp.v12i4.3645 (Year: 2011).*

Hwang, U.-J., Jo, K., Lim, Y. K., Kwak, & Kim, S. (2016). A new method and device of aligning patient setup lasers in radiation therapy. Journal of Applied Clinical Medical Physics, 17(1), 49-61. https://doi.org/10.1120/jacmp.v17i1.5527 (Year: 2016).*

Rowshanfarzad, P., Sabet, M., O'Connor, D. J., Greer, P. B. (2011). Verification of the LINAC isocenter for stereotactic radiosurgery using cine-epid imaging and Arc Delivery. Medical Physics, 38(7), 3963-3970. https://doi.org/10.1118/1.3597836 (Year: 2011).*

"A robust Hough transform algorithm for determining the radiation centers of circular and rectangular fields with subpixel accuracy"; Du, W., Yang, J. (Phys. Med. Biol., 54(3), 555-567, 2009).

"A study of Winston-Lutz test on two different electronic portal imaging devices and with low energy imaging"; Ravindran, P.B. (Australasian Physical and Engineering Sciences in Medicine, vol. 39, Issue 3, 677-685, 2016).

"Development and implementation of an EPID-based method for localizing isocenter", Authors: Daniel E Hyer, Christopher J Mart, Earl Nixon. Journal of applied clinical medical physics, vol. 13, No. 6, 2012.

"Isocenter verification for linac-based stereotactic radiation therapy: review of principles and techniques" Rowshanfarzad, P., Sabet, M., O'Connor, D. J., Greer, P. B. (Journal of Applied Clinical Medical Physics, vol. 12, No. 4, 185-195, 2011).

"Multibody dynamics with unilateral contacts"; Pfeiffer, F., Glocker, Ch. pp. 8-13. (Wiley series in nonlinear science, series editors: Nayfeh, A. H. and Holden, A. V., John Wiley & Sons, Inc., New York, 1996).

* cited by examiner

METHOD FOR EPID-BASED VERIFICATION, CORRECTION AND MINIMIZATION OF THE ISOCENTER OF A RADIOTHERAPY DEVICE

TECHNICAL FIELD

The disclosure relates to a method for verification, correcting and minimizing the isocenter of a radiotherapy device, which comprises at least one patient couch rotatable about at least one couch axis, a support arm rotatable about a support arm axis, a radiator head arranged on the support arm for generating a therapy beam, a rotatable collimator, a device for projecting the radiological isocenter and a digital recording system (EPID—electronic portal imaging device) fixed to the support arm for acquiring dose images by means of the therapy beam.

BACKGROUND

In the treatment of tumor diseases by means of ionizing radiation, a major challenge is to administer the therapeutic absorbed dose to the focus of the disease and to spare the neighboring healthy tissue as much as possible. This is achieved by mechanically and dosimetrically precise radiation therapy devices, such as electron linear accelerators, gamma knives, cyber knives, proton and heavy ion accelerator facilities in conjunction with safety margins adapted to machine and patient positioning tolerances in the target volume definition. A central feature of any radiotherapy device is the spatial deviation of the central beam from the ideal point-like location, which is referred to as the "isocenter" or "ideal isocenter." With an ideal radiotherapy device, with which there are no mechanical tolerances, all angle-dependent central beams intersect in such isocenter. Medical electron linear accelerators, which are used in almost every radiation therapy institution for tumor therapy, have at least three rotational degrees of freedom. These include the following:

the support arm angle with a typical value range of −180° to +180°, the collimator angle with a typical value range of −175° to +175° and the isocentric angle of the patient couch with a usual value range of −95° to +95°

For a real radiotherapy device, the isocenter is not a point, but an isocentroid with a spatial extension (hereinafter also referred to as a "spatial isocenter").

The term "centroid" is derived from ellipsoid, which is a body created by rotating an ellipse around one of its axes. The central rays from all combinations of the above angles cut or touch the isocentroid. To determine the global isocentroid of a radiotherapy device, the respective size and position of the individual isocentroids as a function of each individual degree of angular freedom must first be determined. This measurement and verification of isocentroids is also known as the Winston-Lutz test or Winston-Lutz method.

With the Winston-Lutz test, a radiopaque or radiodense measuring body, as the case may be, also known as a Winston-Lutz pointer, which is rigidly coupled to the patient couch of a radiotherapy device, is initially positioned in the radiological isocenter of a radiotherapy device. Such isocenter is displayed or projected, as the case may be, onto the Winston-Lutz pointer by means of fixed, visible line lasers. After the measuring body has been positioned, a flat dose image is produced at various support arm angles, collimator angles and couch angles by means of a digital recording system (EPID) using a square or round irradiation field, which is limited by the block apertures of a collimator, the leaves of a multi-leaf collimator (MLC) or a round collimator additionally mounted on the radiator head, as the case may be. Subsequently, a digital image processing of the produced dose images is carried out, wherein different algorithms are used to determine the spatial position of the central beam relative to the measuring body. The known methods and algorithms are based, for example, on digital high-pass filters, two-dimensional operators for edge amplification and edge detection (such as Sobel operators, Canny filters), line extraction (Hough transform), calculation of the center of mass (signal intensity weighting), convolution method, object segmentation (segmentation, contouring) and the thresholding method. In the review paper entitled "*Isocenter verification for linac-based stereotactic radiation therapy: review of principles and techniques*," Rowshanfarzad, P., Sabet, M., O'Connor, D. J., Greer, P. B. (Journal of Applied Clinical Medical Physics, Volume 12, No. 4, 185-195, 2011), the aforementioned methods are explained and their advantages and disadvantages are discussed. The main disadvantages of EPID-based methods for isocenter verification compared to film-based methods consist of the comparatively lower resolution capacity, which makes an exact verification of the radiological isocenter more difficult. In a recent publication entitled "*A study of Winston-Lutz test on two different electronic portal imaging devices and with low energy imaging*," Ravindran, P. B. (Australasian Physical and Engineering Sciences in Medicine, Volume 39, Issue 3, 677-685, 2016), the Winston-Lutz pointer is moved in real time with the minimum step size of 0.25 mm. As can be seen from this, a maximum error of 0.04±0.02 mm in the central beam distances from the Winston-Lutz pointer is determined by means of morphological operations. From the publication entitled "*A robust Hough transform algorithm for determining the radiation centers of circular and rectangular fields with subpixel accuracy*," Du, W., Yang, J. (Phys. Med. Biol., 54(3), 555-567, 2009), it is known that a theoretical accuracy of 0.02±0.01 mm can be achieved by means of a Hough transform in mathematically varied dose images, wherein machine tolerances are not taken into account.

Further problems of the known methods consist of the impossibility of carrying out measurements with certain support arm angle/couch angle combinations and an unfavorable signal/noise ratio.

With EPID-based methods, there is still the problem that evaluation methods such as the Hough transform are unsuitable for MLC-shaped irradiation fields, since the leaves cannot form straight field limits with their ends, due to finite positioning accuracy and transmitted radiation between the leaves.

Another disadvantage is that the positioning inaccuracies of the recording system in all EPID-based methods—in particular a violation of the orthogonality to the central beam and an inaccurate distance to the isocenter—influence the result. Further shortcomings of the known EPID-based methods are a lack of representation of the global isocentroid, in which the central beam deviation from the ideal isocenter is apparent for any combination of the three angles for the support arm, collimator and patient couch, a lack of a mathematical description of the global isocentroid to minimize it by means of optimizing parameters of the radiotherapy device, and a lack of investigations of the influence of all measurement conditions on the result.

SUMMARY

The object underlying the present invention is now to propose an EPID-based method for verifying and correcting the isocenter of a radiotherapy device, with which the disadvantages known from the prior art can be avoided or reduced.

The task is achieved by a method as claimed.

In accordance with the task definition, a method for the EPID-based verification, correction and minimization of the isocenter of a radiation therapy device, which comprises at least one patient couch rotatable about a couch axis, a support arm rotatable about a support arm axis, a radiator head arranged on the support arm for generating a therapy beam, a rotatable collimator, a device for projecting the radiological isocenter and a digital recording system (EPID) for acquiring dose images by means of the therapy beam, is proposed, the procedure for which is as follows:

a) a measurement body is positioned, by means of the projection device, at the projection position in the current radiological isocenter of the radiotherapy device, b) an irradiation field, limited by the collimator, is applied for at least one predefined angular setting of the support arm, the patient couch and the collimator and thereby c) at least one common dose image of the measurement body and the irradiation field is captured using the EPID, d) a dose profile for each direction within an EPID coordinate system is created on the basis of the captured dose image and e) in the plot of the dose profile an inflection point between a local dose minimum and a local dose maximum, and between a local dose maximum and a local dose minimum is determined at each of both expected bodily limits of the measuring body in the X-direction of the EPID coordinate system and at each of the two expected bodily limits of the measuring body in the Y-direction of the EPID coordinate system, and f) the determined positions of the inflection points are linked to the bodily limits of the measurement body in the X-direction and in the Y-direction, g) the position of the center point of the measurement body relative to the EPID-center is determined in the dose image on the basis of the linked bodily limits of the measurement body, the steps d) tog) being carried out in the same way for the field limits and the field center point of the irradiation field, that is, a dose profile is created on the basis of the recorded dose image and, in the plot of the dose profile an inflection point between a local dose minimum and a local dose maximum, and between a local dose maximum and a local dose minimum is determined at each of both expected field limits of the irradiation field in the X-direction of the EPID coordinate system and at each of the two expected field limits of the irradiation field in the Y-direction of the EPID coordinate system, and the determined positions of the inflection points are linked to the field limits of the irradiation field in the X-direction and in the Y-direction and a position of the field center point of the irradiation field relative to the EPID center is determined in the dose image on the basis of the linked field limits of the irradiation field, h) a differential vector is determined from a deviation in position of the center point of the measurement body from the EPID-center and from a deviation in position of the field center point of the irradiation field from the EPID-center, and i) the vector components of the differential vector are used to correct the current radiological isocenter.

In step d), a change of unit from pixel to mm can be made to determine absolute distances. The change of unit represents a transition from digital to analog dose profile, such that the further processing of the geometry data in an algorithm can be ensured.

The coordinate system essential for the measurement setup and for the performance of the method is the inertial system (spatially fixed radiotherapy device coordinate system), in which the isocenter deviations (central beam deviations from the ideal isocenter) are specified. The inertial system has the ideal isocenter ISO (center point of the measuring body or the tungsten sphere of the Winston-Lutz pointer, as the case may be) as its origin. Since the coordinate system of the recording device used for steps c) to h) and the collimator coordinate system are movable, coordinate transformations are required. Upon the variation of the support arm angle (G), the respective difference vector is mapped into the inertial system by means of the left matrix in the equation (5) listed below, where $\beta=G$. Upon the variation of the collimator angle (C), prior to analysis, the dose images are mapped into the EPID coordinate system using the right matrix in equation (5), where $\gamma=-C$; after analysis, the vectors are mapped into the inertial system using the same matrix, where $\gamma=C$. Upon the variation of the patient couch angle (T) with $G \neq 0°$, the left matrix in equation (5) with $\beta=G$ is again necessary for coordinate transformation. Since errors occur in the result due to machine tolerances—in particular, positioning errors of the recording system—all difference vectors are mapped from the real to the ideal coordinate system according to equation (2) below before mapping into the inertial system. The EPID coordinate system, which is positioned in a manner fixed to the support arm and has its origin in the central detector element of the EPID, is also relevant. Preferably, the projection of the current radiological isocenter takes place by means of five spatially fixed line lasers. Crosshairs, which can be in the form of colored notches on the surface of the measuring body, allow the measuring body to be positioned exactly in the projected isocenter of the radiotherapy device.

According to an advantageous additional form of the method, the method steps b) to h) can be carried out for the degrees of angular freedom of the patient couch, the support arm and the collimator with an increment of a maximum of 30°. Thereby, it is also expedient to be able to select angle settings that are relevant for subsequent treatment of a patient.

It can also be provided that difference vectors obtained from dose images taken from different angular positions of the patient couch, support arm and collimator are used to determine the size and location of the spatial isocenters, wherein the vector components of the spatial isocenter location vectors are used to correct the radiological isocenter.

The method can preferably be carried out automatically using an appropriate software program. An automatic execution of steps d) to i) and in particular an evaluation of dose profiles to find inflection points along with the execution of coordinate transformations can take place by means of routines, for example in the MATLAB® software package.

Preferably, in step e), the dose profile of the dose image in the X-direction and in the Y-direction can be examined for inflection points between a dose minimum and a dose maximum and in the further plot between a dose maximum and a dose minimum, in order to determine all bodily limits of the measuring body and limits of the irradiation field. Ideally, the measuring body is a tungsten sphere with a diameter of between 5 mm and 10 mm. Thereby, it should be noted that the parameter values found in the failure mode and effect analysis for suitable measurement and analysis conditions are preferably valid for a sphere diameter of 5 mm. However, the method is not to be limited to a spherical measuring body for carrying it out. Therefore, other body shapes of the measuring body are also conceivable.

According to one embodiment, the two-dimensional image of the diameter of a spherical measuring body and the field width of an irradiation field in the dose image corresponds to the distance between two inflection points in the dose profile parallel to the X-direction of the aperture coordinate system fixed to the collimator. Thereby, inflection points can be considered as those points that have exactly 50% of the absorbed dose of the field center in the dose image. Accordingly, in the Y-direction. those points which show exactly 50% of the absorbed dose of the field center in the dose image can be considered as inflection points. The inflection points that are thereby determined are linked to the field limits of the irradiation field. Since, in the area of the two-dimensional field center, the local dose minimum is located behind the measuring body, the smallest of the local dose maxima of the dose profiles in the X-direction and the Y-direction can be used as a substitute for the 100% dose. The determination of the bodily limits of the measuring body takes place analogously. The absorbed dose for defining the limits of the spherical measuring body is the arithmetic mean arising from the 100% substitute dose and the local dose minimum behind the sphere, thus a 50% substitute dose. The dose maxima are located between the spherical measuring body and the field limits that are defined by the collimator setting. In accordance with the preceding statements, it can also be provided that the inflection point(s) is/are determined in the range of a 50% dose point between a dose minimum and a dose maximum and/or between a dose maximum and a dose minimum of the dose profile. The definition of the field size and central beam position using the 50% isodose is described in the IEC 60976 standard.

The measurement planes perpendicular to the image plane, which cut out the corresponding dose profiles to define the field size, the central beam and the sphere size and of the sphere center point, can be determined automatically with the assistance of a software program using an algorithm. Starting from the local dose minimum in the dose image of the spherical measuring body, which lies approximately in the image center, two orthogonal measuring planes can be defined in a first iteration step. The dose profiles that are thereby determined are analyzed with respect to field size, central beam position, sphere size and sphere center point. In the second iteration step, the symmetry lines of the irradiation field and the spherical measuring body can be determined with the determined central beam position and the determined sphere center point of the measuring body. In the case of irradiation fields limited by means of a circular collimator and upon the determination of the sphere center point of the measuring body, the lines of symmetry are identical with the lines of intersection of the measuring planes. The analysis of the dose profiles described above or the linking of inflection points to bodily limits and field limits, as the case may be, provides the distances of the central beam penetration point and the sphere center point of the measuring body in the image plane relative to the EPID center.

It has been shown that, with the method, a spatial resolution of 0.01 mm for the spatial deviation of the central beam from the spherical measuring body can be achieved in the definition of the field size, the central beam position, the sphere diameter and the center point of the spherical measuring body, which can be verified by measurement technology. For example, a method-related resolution of 0.01 mm could be achieved when using an EPID with a pixel size of 0.392 mm. This can be achieved by considering a section of the inflectional tangent of the dose profile in the area of the 50% dose point for the exact determination of the field limits or the bodily limits of the spherical measuring body, as the case may be. In this area of the dose profile, the inflectional tangent is the best approximation of the dose curves over the spatial coordinates. The approximation with the smallest error can be achieved with the shortest tangent that can still be displayed in the digital dose image with a discrete pixel size. In the direction of the spatial coordinate, it measures exactly one pixel—or as a special case, two pixels—if the 50% dose point coincides exactly with a pixel center. Thereby, the two pixels in the area of the 50% dose point are determined, one of which has a lower and one a higher gray value than the 50% dose point. In doing so, if the pixel size is known, a concrete distance can be determined. The exact spatial coordinates for the field limits of the irradiation field and the bodily limits of the spherical measuring body can be obtained by linear interpolation between the two grayed pixels.

In accordance with the advantageous design variant of the method, it can be provided that the inflection point(s) in the area of the 50% dose point is/are preferably defined between two pixels, of which a first pixel represents a dose lower than 50% and a second pixel adjacent to the first pixel represents a dose higher than 50%.

Finally, the difference vector is imaged as a displacement vector between the central beam penetration point and the center point of the spherical measuring body, measured in the EPID plane, by means of a scaling into the isocenter plane, wherein the stretch center is the beam focus and the stretch factor according to $$k = \frac{SAD}{SID} < 1 \; mit \; SAD = 1m \qquad \text{equation (1)}$$

depends on the constant "focus-axis distance" SAD and the variable "focus-EPID distance" SID. In addition, the position vectors dependent on the support arm angle are mapped from the image plane into the spatially fixed coordinate system of the radiotherapy device by means of a coordinate transformation. The orientation of such inertial system is specified in the IEC 61217 standard.

According to an additional conception, the position vectors of the spatial isocenters are used for the calibration of a patient positioning system. Alternatively or in addition, it can be provided that the position vectors of the spatial isocenters are used to correct the projection device in order to be able to adjust the laser projection of the radiological isocenter. The position vector of the isocentroid is understood to be the spatial center position of the isocentroid.

The advantage of the method lies in particular in the extraction of a dose profile with the unit of length millimeter from a dose image with the unit of length of the pixel, such that this can be processed with less computational effort in a shorter time and in particular with computationally higher resolution. The advantage of this is that a majority of the known radiotherapy devices have a possibility for digital recording (EPID) of an irradiation field anyway, such that isocenter verification and a corresponding correction can be carried out with little effort using existing devices. Thus, due to the comparatively short time required to carry out and automatically analyze the method, it is possible that an isocenter verification (verification of the isocenter) can be carried out immediately prior to a radiosurgical application, in order to ensure the best possible patient safety. Furthermore, it has been shown that, using the method, a calculated resolution of 0.01 mm can be achieved without the need for technical modifications to the equipment, such as high-resolution recording systems. In summary, with an isocenter verification carried out according to the method, increased patient safety can be achieved with already existing radiation therapy devices with EPID. Since comparatively less time is required to carry out isocenter verification and isocenter correction using the method, costs can also be saved.

For further optimization, in accordance with an additional form of the method, it can be provided that a correction of machine tolerances is undertaken. For example, a correction of the $_{EPID}r'_i$ position vectors in the EPID coordinate system can be provided. If the EPID is incorrectly positioned, a further transformation step from the shifted EPID coordinate system to the ideal EPID coordinate system may be required to correct the $_{EPID}r'_i$ position vectors:

$$_{EPID}r'_i = A_{korr} \cdot _{EPID}r'_i, \quad \text{equation (2)}$$

where the correction matrix $$A_{korr} = A_\gamma \cdot A_\beta \cdot A_\alpha \in \mathbb{R}^{3,3} \quad \text{equation (3)}$$

is the product of three elementary rotations. According to the calculation rule of "multiply vectors with matrices from the left," the sequence of rotations is defined as for cardan angles: angle α around the X-axis, angle β around the Y-axis and angle γ around the Z-axis. Since, with a radiotherapy device, all angle errors are ≤1° after its acceptance test, the sequence of rotation has no influence on the correction, and the following applies to a general angle α: sin α≈ tan α≈α ∧ cos α≈1 with α in radian measure. For a rotation around the X-axis of the ideally positioned EPID, the right imaging matrix in equation (3)

$$A_\alpha = \begin{pmatrix} 1 & 0 & 0 \\ 0 & \cos\alpha & -\sin\alpha \\ 0 & \sin\alpha & \cos\alpha \end{pmatrix} \quad \text{equation (4)}$$

is a function of the angular deviation a. Accordingly, in equation (3), the rotation matrices around the Y-axis and Z-axis $$A_\beta = \begin{pmatrix} \cos\beta & 0 & \sin\beta \\ 0 & 1 & 0 \\ -\sin\beta & 0 & \cos\beta \end{pmatrix}, \, A_\gamma = \begin{pmatrix} \cos\gamma & -\sin\gamma & 0 \\ \sin\gamma & \cos\gamma & 0 \\ 0 & 0 & 1 \end{pmatrix} \quad \text{equation (5)}$$

depend on the corresponding angular deviations β and γ. The definition of the cardan angles and the mapping matrices in equations (4) and (5) can be found, for example, in "*Multibody dynamics with unilateral contacts*," Pfeiffer, F., Glocker, Ch. (Wiley series in nonlinear science, series editors: Nayfeh, A. H. and Holden, A. V., John Wiley & Sons, Inc., New York, 1996). Translational corrections do not have to be applied, because the sought-after difference vector $$r_{ISO} = r_{CAX} - r_{WLP} \in \mathbb{R}^3 \quad \text{equation (6)}$$

between the penetration point $r_{CAX}$ of the central beam and the spherical center $r_{WLP}$ of the measuring body does not depend on displacements of the EPID in its X-Y plane. The tolerance of the vertical coordinate is taken into account in the scaling of the image plane to the isocenter plane by the corrected focus-EPID distance in equation (1). The tolerances of the three degrees of angular freedom can also be taken into account. Deviations measured for the support arm angle, the collimator angle, and the couch angle can be taken into account by using an appropriate software program by input, wherein they contribute to error correction as part of an algorithm.

With radiosurgery and stereotactic precision irradiation, rectangular or square, as the case may be, irradiation fields are usually not used because of irregular structures of the tissue to be irradiated. In such cases, the irradiation fields are limited by the leaves of a multileaf collimator (MLC). According to one design variant of the method, with which an MLC is used, the central beam positions between several pairs of leaves of an MLC are therefore determined in the X-direction. Thus, when using an MLC, it can be provided that steps d) to h) of the method are carried out for each pair of leaves of the MLC limiting the irradiation field. It can also be provided that the outer pairs of leaves are not used for the analysis, since, there, the dose gradients are disrupted by scattering photons from the aperture system to the field limitation in the Y-direction.

In order to determine the central beam position in the Y-direction, two dose profiles are evaluated for irradiation fields formed by block apertures or the MLC, which are cut out in mirror image to the symmetry line of the X-coordinate. The mirror-symmetrical measuring planes along with the arithmetic averaging of the individual central beam positions in both directions X and Y have the advantage that possible angular errors of the collimator are, in the result, compensated for by averaging. A further advantage is that less field disturbances are caused by the measuring body, since the interesting 50% dose points in the dose profiles are at a greater distance from the measuring body or the Winston-Lutz pointer, as the case may be.

In accordance with an additional advantageous design variant of the method, a support arm angle≠0° is set upon a variation of the patient couch angle, in order to obtain a statement regarding the vertical positional change of the measuring body. Preferably, a support arm angle of 30° is set upon a variation of the angle of the patient couch, wherein an angle of the patient couch in the range between 0° and 90° is possible. In the same manner, a support arm angle of –30° enables an angle of the patient couch in the range between 0° and –90°. Alternatively, in the event that a fixed patient positioning system independent of the radiotherapy unit is used, the isocentroid of the couch can be determined without moving the support arm. With the above variant, the couch angle variation is carried out with the discrete angles (–90: 30:90)°. The position of the support arm is 0°, such that the radiator head is not located in the two useful radiation fields of the external X-ray system. In the event that the ExacTrac 6.0.6 (BRAINLAB AG, Feldkirchen, Germany) patient positioning system is used, at each set couch angle, the spatial position of the measuring body, which may be a Winston-Lutz pointer from BRAINLAB AG (Feldkirchen, Germany), is radiologically determined in the verification step of "Detect Winston-Lutz Pointer" with the functionality of "Winston-Lutz Pointer Analysis." The negative values of the displacements of the measuring body relative to the ideal isocenter of the radiotherapy device are stored vectorially in the file WL_Test.log. This comprises data in the form of a text document that can be read by the MATLAB® software package. In the file data, the columns 15-17 contain the displacement vector dependent on the couch angle $$[-WLshiftLat, -WLshiftLong, -WLshiftVert] \quad \text{equation (7)}$$

which in the initial system has the form $$r_{ET}(T) = \begin{pmatrix} X_{ET} \\ Y_{ET} \\ Z_{ET} \end{pmatrix} = -\begin{pmatrix} WLshiftLat \\ WLshiftLong \\ WLshiftVert \end{pmatrix} \quad \text{equation (8)}$$

The offset $$r_0 = \begin{pmatrix} \Delta X_{CAX}(G = 0° \wedge T = 0°) \\ \Delta Y_{CAX}(G = 0° \wedge T = 0°) \\ \Delta Z_{CAX}(G = 0° \wedge T = 0°) \end{pmatrix} \quad \text{equation (9)}$$

of the central beam from the ideal isocenter of the radiotherapy device is known from the determination of the isocentroid dependent on the support arm angle, and does not change with the couch angle. Thus, the displacement vector (distance vector) of the central beam from the measuring body is the vector sum $$\Delta r_{CAX}(T) = r_{ET}(T) + r_0, \quad \text{equation (10)}$$

which describes the isocentroid of the patient couch in the inertial system.

In accordance with an additional form of the method, a global isocentroid can be determined from the individual deviations in the three spatial directions X, Y and Z. The procedure is as follows: After, for each degree of angular freedom, the geometry of the isocentroid has been determined with the characteristics Deviations of the central ray from the Winston-Lutz pointer in the three spatial directions X, Y and Z as a function of an angle,
  Radial absolute deviation of the central beam from the Winston-Lutz pointer as a function of an angle,
  Spatial coordinates of the isocentroid,
  Maximum diameter of the isocentroid in the three spatial directions and
  Maximum global radius of the isocentroid in the spatially fixed coordinate system (inertial system), a global isocentroid can be determined with all results. This can be achieved by considering the angle-dependent measurement conditions in a summarized form:

The isocentroid of the support arm is determined at a 0° collimator and couch angle.
  The isocentroid of the collimator is determined at a 0° support arm and couch angle.
  The isocentroid of the couch is determined halfway with a 30° or −30°, as the case may be, support arm angle and halfway with a 0° collimator angle.

Based on the isocentroid representation as a function of the support arm angle, the additional maximum possible isocenter deviations due to collimator angle variation and couch angle variation can be represented as scatter bands in a positive and negative direction over the support arm angle. The evaluation regarding the spatial coordinates and maximum diameter or the largest radius, as the case may be, is conclusively updated. In addition, the center distances, which according to the standard DIN 6875—Part 2 must be measured at least every six months, are determined between all three axes of rotation. The scattering bands have a negative and positive component. For the isocenter deviations of the collimator angle variation, their determination first of all requires a mapping from the EPID coordinate system into the initial coordinate system:

$$r_{ISO}(G,C) = A_\beta \cdot {}_{EPID}r_{ISO}(C). \quad \text{equation (11)}$$

The mapping matrix is known from equation (5), where $\beta = G$ is the support arm angle. The position vector $$r_{ISO} = \begin{pmatrix} X_{ISO} \\ Y_{ISO} \\ Z_{ISO} \end{pmatrix} \quad \text{equation (12)}$$

is composed of the components of the isocenter deviation. The negative scatter bands result in $$\Delta X^-_{ISO}(G) = \min_{C \in [-175°, +175°]} [X_{ISO}(G, C)] - X_{ISO}(G, C = 0°), \quad \text{equation (13)}$$

$$\Delta Y^-_{ISO}(G) = \min_{C \in [-175°, +175°]} [Y_{ISO}(G, C)] - Y_{ISO}(G, C = 0°), \quad \text{equation (14)}$$

$$\Delta Z^-_{ISO}(G) = \min_{C \in [-175°, +175°]} [Z_{ISO}(G, C)] - Z_{ISO}(G, C = 0°). \quad \text{equation (15)}$$

Accordingly, the positive scattering bands are obtained in accordance with $$\Delta X^+_{ISO}(G) = \max_{C \in [-175°, +175°]} [X_{ISO}(G, C)] - X_{ISO}(G, C = 0°), \quad \text{equation (16)}$$

$$\Delta Y^+_{ISO}(G) = \max_{C \in [-175°, +175°]} [Y_{ISO}(G, C)] - Y_{ISO}(G, C = 0°), \quad \text{equation (17)}$$

$$\Delta Z^+_{ISO}(G) = \max_{C \in [-175°, +175°]} [Z_{ISO}(G, C)] - Z_{ISO}(G, C = 0°). \quad \text{equation (18)}$$

Preferably, the interval of the collimator angle for the search for extremes can be defined in equations (13) to (18) with $C \in [-90°, +90°]$, since all optimal collimator angles for patient treatment lie in this range. The scattering bands for the couch angle variation are obtained analogously to equations (13) to (18), by defining the collimator angle C by the couch angle T and the intervals for the search for extremes by means of $T \in [-90°, +90°]$.

Within the scope of the method, isocentroids can be minimized by optimization. Minimization through optimization is conceivable for Isocentroid of the support arm in the event that a round collimator and an external patient positioning system is used,
  Combined isocentroid of the support arm and the collimator in the event that a patient positioning system is used,
  Combined isocentroid of the support arm and the patient couch in the event that a round collimator without a patient positioning system is used, and/or
  Global isocentroid in the event that neither a round collimator nor a patient positioning system is available.

If an independent radiological patient positioning system is used in conjunction with the radiotherapy unit, the isocentroid of the patient couch can be disregarded, since all central beam deviations dependent on the couch angle are detected and corrected by the isocentroid. When using round collimators, the collimator angle C is usually $C = 0° = $ constant.

When limiting the field with an MLC, the optimization variables in the vector $$x_O = \begin{pmatrix} x_{CLO} \\ y_{JO} \\ 0 \end{pmatrix} \in \mathbb{R}^3 \qquad \text{equation (19)}$$

can be combined, where $x_{CLO}$ is the centerline offset of the leaves and $y_{JO}$ is the jaw offset of the Y-aperture pair. The first component of such vector can also be the jaw offset of the X-aperture pair, if the irradiation field is to be limited. The second component can also be identical with 0 if the field limitation in the Y-direction is achieved solely by the leaves of the MLC. When using round collimators, equation (19) contains their offsets. The isocentroids listed above, that is, the isocentroid of the support arm, the combined isocentroid of the support arm and the collimator, the combined isocentroid of the support arm and the patient couch and the global isocentroid, are functions of the support arm angle G. The solitary support arm isocentroid is composed of the components.

$$r_{ISO}(G) = \begin{pmatrix} X_{ISO}(G) \\ Y_{ISO}(G) \\ Z_{ISO}(G) \end{pmatrix} \qquad \text{equation (20)}$$

The combined isocentroids can be described in each spatial direction by two functions that limit them in the negative direction and in the positive direction, as the case may be:

$$r_{ISO}^-(G) = \begin{pmatrix} X_{ISO}^-(G) \\ Y_{ISO}^-(G) \\ Z_{ISO}^-(G) \end{pmatrix}, \qquad \text{equation (21)}$$

$$r_{ISO}^+(G) = \begin{pmatrix} X_{ISO}^+(G) \\ Y_{ISO}^+(G) \\ Z_{ISO}^+(G) \end{pmatrix} \forall C,$$

$T \in [90°, +90°]$.

The collimator angle C and the couch angle T of the patient couch can be varied within the specified interval. The value range of the collimator angle C can be limited to $\pm 90°$, since it is typically the case that all optimal collimator angles lie in this range.

According to an additional advantageous design variant of the method, it can be provided that all device-specific parameters influencing the spatial isocenters are optimized by applying one or more predetermined target function(s). Thus, a correction of machine parameters can be provided. Advantageously, the optimization can be carried out by means of software. Possible target functions that can be used for optimization, which depend on the variables in equation (19), concern the sums, arithmetic averages, extremes and integrals over the support arm angle of the squares of Distances $X^-_{ISO}(G_i)$, $Y^-_{ISO}(G_i)$, $Z^-_{ISO}(G_i)$, $X^+_{ISO}(G_i)$, $Y^+_{ISO}(G_i)$, $Z^+_{ISO}(G_i)$, Spatial radii $R_{ISO}(G_i) = \sqrt{X_{extr}^2(G_i) + Y_{extr}^2(G_i) + Z_{extr}^2(G_i)}$ Diameters $D_X(G_i)$, $D_Y(G_i)$ and $D_Z(G_i)$ of the isocentroid under examination at discrete support arm angles $G_i \in [-180°, +180°]$.

The following applies to the components of the spatial radius:

$$K_{extr}(G_i) = \max[|\min[K_{ISO}^-(G_i)]|, |\max[K_{ISO}^+(G_i)]|] \text{mit}$$
$$K \in \{X, Y, Z\} \qquad \text{equation (22)}$$

at the discreet support arm angle $G_i$.

The definition of the diameter is $$D_K(G_i) = K_{ISO}^+(G_i) - K_{ISO}^-(G_i) \text{ mit } K \in \{X, Y, Z\} \qquad \text{equation (23)}$$

In the special case of the solitary isocentroid of the support arm, the geometric quantities that can be optimized are defined as follows:

The distances $X_{ISO}(G_i)$, $Y_{ISO}(G_i)$ and $Z_{ISO}(G_i)$.

The spatial radii $$R_{ISO}(G_i) = \sqrt{X_{ISO}^2(G_i) + Y_{ISO}^2(G_i) + Z_{ISO}^2(G_i)}$$

The maximum diameter $$D_K(G_i) = \max_{G_i}[K_{ISO}(G_i)] - \min_{G_i}[K_{ISO}(G_i)]$$

with $K \in \{X, Y, Z\}$. With the three geometric quantities and four functions each, twelve different target functions can be selected for optimization, wherein some target functions are redundant with respect to optimization:

$$\sum_{K \in \{X,Y,Z\}} \left[ \int_{-G_i} [K_{ISO}^+(G_i) - K_{ISO}^-(G_i)]^2 dG \right] \equiv \sum_{K \in \{X,Y,Z\}} \left[ \int_{G_i} D_K^2(G_i) dG_i \right]$$

$$\sum_{G_i} R_{ISO}^2(G_i) \equiv \operatorname*{mean}_{G_i}[R_{ISO}^2(G_i)],$$

$$\sum_{G_i} [D_X^2(G_i) + D_Y^2(G_i) + D_Z^2(G_i)] \equiv \sum_{K \in \{X,Y,Z\}} \left[ \operatorname*{mean}_{G_i}[D_K^2(G_i)] \right]$$

When searching for the best optimization for a specific irradiation task, it is therefore not necessary to consider all target functions, since the functions of each of the pairs mentioned here provide identical results.

During optimization, the position vector of the central beam deviations in equation (6) varies in accordance with $$r'_{CAX} = r_{CAX} + x_O \in \mathbb{R}^3 \qquad \text{equation (24)}$$

in the detector coordinate system (EPID coordinate system). Equations (5) and (6) can be used to determine the spatial deviations of the isocentroids under examination in the spatially fixed coordinate system of the radiotherapy device. Thereby, in equation (5), the angles $\beta = G$ and $\gamma = C$ are to be replaced by the support arm angle or the collimator angle, as the case may be.

The vector $x_O$ is optimal if for one of the target functions outlined above, which contains the variables of equation (19) in quadratic form, applies:

$$f(x_O) = \text{Minimum!} \qquad \text{equation (25)}$$

To adjust the collimator parameters on a radiotherapy device, the optimized parameters in equation (19) can then be selected from the various solutions. For example, those can be selected that minimize the mean spatial radius $$\int_{G_i} R_{ISO}(G_i) dG \qquad \text{equation (26)}$$

of the central beam. For the systematics of proportional, identical safety spaces in all spatial directions, with which a tumor volume is expanded to the irradiation volume, such that a tumor can be completely irradiated even with positioning inaccuracies, tumor mobility and machine tolerances, only the maximum diameter of the relevant isocentroid would be minimized:

$$\max_{G_i}[D_X(G_i), D_Y(G_i), D_Z(G_i)].\qquad\text{equation (27)}$$

To solve the nonlinear optimization task without constraints in equation (25), the subroutine fminsearch can be used in MATLAB®. The calculation scheme that is thereby used is a simplex algorithm of the Nelder-Mead type for direct minimum search.

Furthermore, it can be provided that, according to an advantageous design variant of the method, geometric tolerances of the radiotherapy device are quantified and taken into account in the calculation.

According to an additional advantageous design variant of the method, it can be provided that the irradiation field is applied taking into account suitable values of a field size, a relaxation time of the support arm, an energy-dependent dose per irradiation field, and/or a focus-EPID distance.

Furthermore, an application of the method on a therapy simulator can be provided, wherein the spatial isocenters are determined, corrected and minimized.

BRIEF DESCRIPTION OF THE DRAWINGS

The invention is to be described in more detail by way of example on the basis of the following figures.

The following are shown.

DETAILED DESCRIPTION

Figure 1:
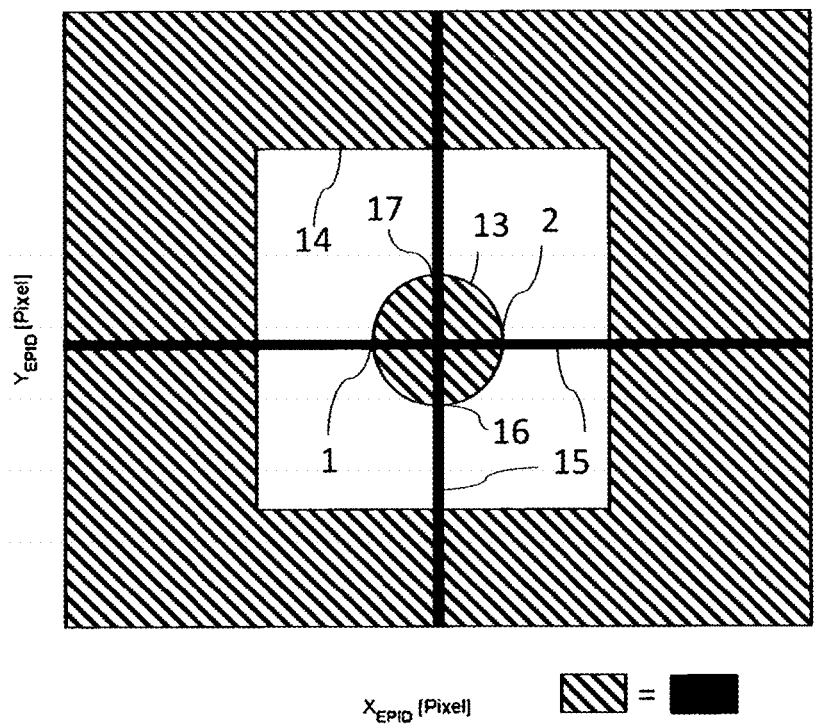
FIG. 1 a two-dimensional dose image of a spherical measuring body in an MLC-limited irradiation field, FIG. 2a a dose profile of a two-dimensional dose image for explaining an exemplary embodiment of the method, FIG. 2b the dose profile from FIG. 2a for explaining the definition of the 50% dose points, FIG. 3 a schematic diagram for the verification in terms of measurement technology of the achieved spatial resolution, FIG. 4 dose profiles of the Winston-Lutz pointer as the measuring body, FIG. 5 additional dose profiles of an MLC-limited irradiation field in the X-direction, FIG. 6 additional dose profiles of an MLC-limited irradiation field in the Y-direction, FIG. 7 a schematic diagram of the geometry of an isocentroid dependent on the support arm angle of a radiotherapy device, FIG. 8 a graphical representation of a global isocentroid.
Figure 2A:
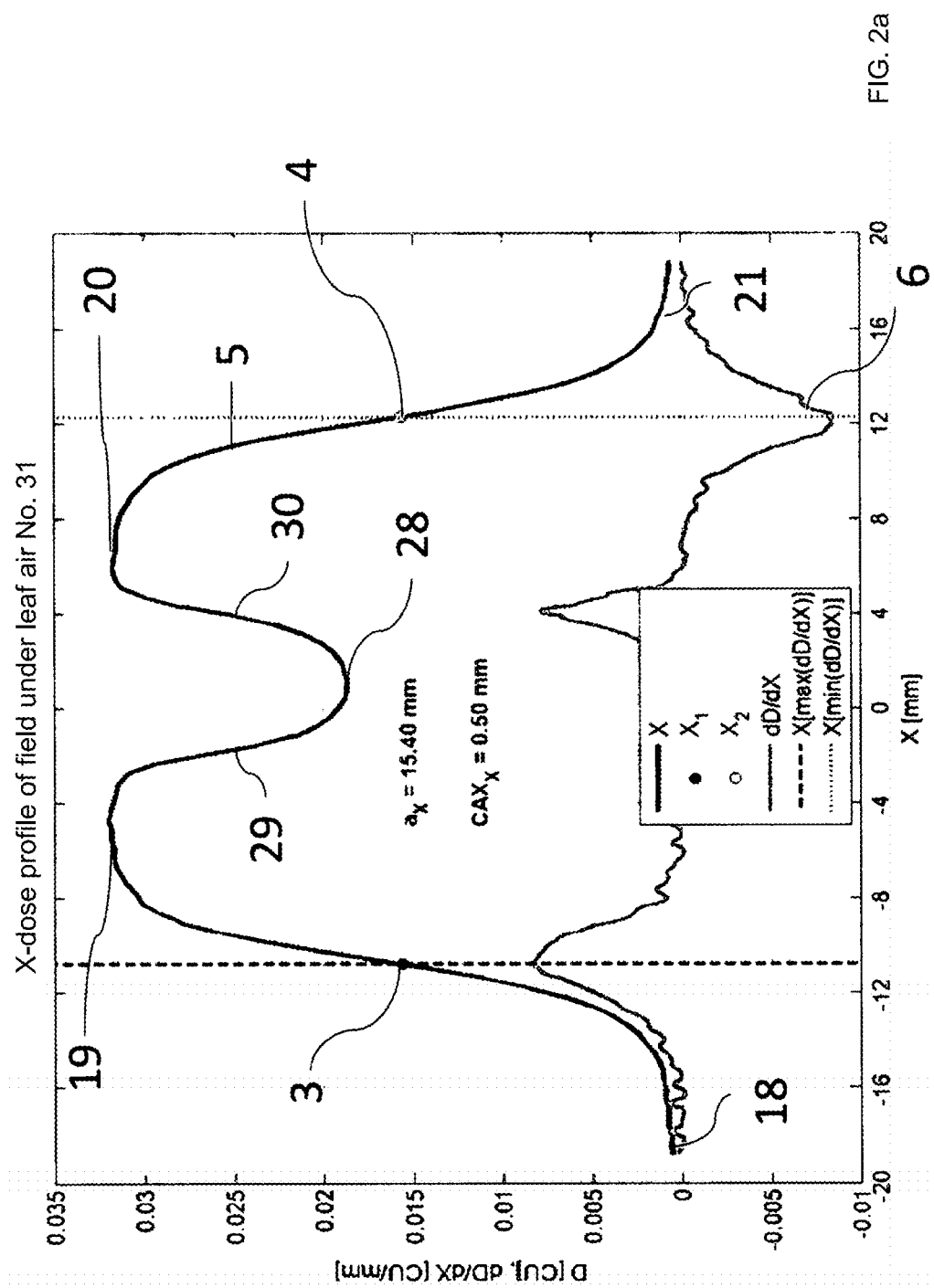
Figure 2B:
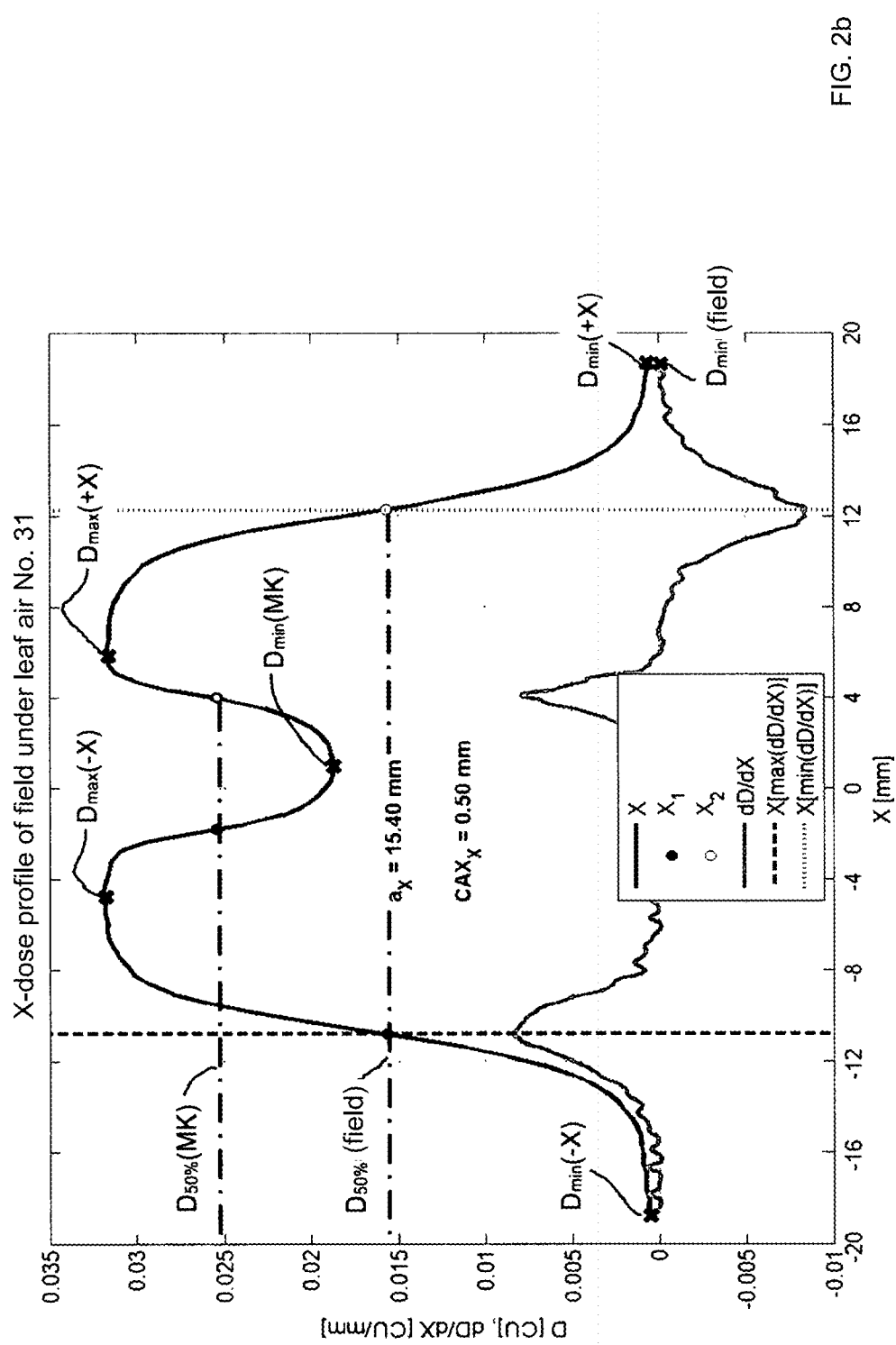

For explaining the method, FIGS. 1, 2a and 2b are to be considered together.

With the method for the EPID-based verification and correction of the isocenter of a radiotherapy device, which comprises at least one patient couch rotatable about at least one couch axis, a support arm rotatable about a support arm axis, a radiator head arranged on the support arm for applying the therapy beam, a collimator for limiting a radiation field, a device for projecting the radiological isocenter and a digital recording system (EPID) for generating dose images by means of the therapy beam, the following steps are carried out:

a) A measuring body 13 is positioned at the projection position of the radiological isocenter of a radiotherapy device, b) Subsequently, an irradiation field is applied for at least one predetermined angle setting of the support arm, the patient couch and the collimator, and thereby c) Using the EPID, a dose image of the measuring body 13 is taken, as shown in FIG. 1. The dose image in FIG. 1 comprises a two-dimensional grayscale dose image of an MLC-limited irradiation field of 15×15 mm² in MATLAB® (version R2007a). The EPID used has pixels with an edge length of 0.392 mm. The reference sign 13 indicates a spherical measuring body (Winston-Lutz pointer) with a known diameter. The reference sign 14 indicates a limit of the irradiation field caused by the collimator. In the dose image, dark areas have a lower applied absorbed dose compared to light areas. To determine the sphere center point of the measuring body 13 by means of the crossed, orthogonal measuring planes 15, initially, both sphere boundaries 1 and 2 are determined in the X direction and both sphere boundaries 16 and 17 are determined in the Y direction. The sphere boundaries 1, 2, 16 and 17 can be determined from the dose profiles, which are generated on the basis of the recorded dose image in step (d) of the method. FIG. 2a and FIG. 2b show a dose profile 5 in the X-direction of the dose image shown in FIG. 1. The curve marked with the reference sign 6 in FIG. 2a represents the gradient of the dose profile over the X-axis.

Further in step e) of the method, initially, a central position of the measuring body 13 is determined by calculating, in the plot of the dose profile 5, at at least one expected limit of the measuring body 13, an inflection point 29 between a dose maximum 19 and a dose minimum 28, and an inflection point 30 between a dose minimum 28 and a dose maximum 20. The inflection points 29 and 30 can be determined in the area of the 50% dose point, wherein the 50% dose point comprises the position in the plot of dose profile 5, at which the dose is 50% between the dose minimum 28 and the dose maxima 19 and 20. Preferably, the 50% dose point is determined between two pixels, of which a first pixel represents a dose less than 50%, and a second pixel adjacent to the first pixel represents a dose greater than 50%.

An analogous procedure can be used to determine the field limits of the irradiation field, wherein, in the plot of the dose profile 5, at at least one expected limit of the irradiation field, an inflection point 3 is determined between a dose minimum 18 and a dose maximum 19, and an inflection point 4 is determined between a dose maximum 20 and a dose minimum 21. The inflection points 3 and 4 can be determined in the area of the 50% dose point, wherein the 50% dose point comprises the position in the plot of dose profile 5, at which the dose is 50% between the dose minima 18 and 21 and the dose maxima 19 and 20. Preferably, the 50% dose point is determined between two pixels, of which a first pixel represents a dose less than 50% and a second pixel adjacent to the first pixel represents a dose greater than 50%.

In the subsequent step f) of the method, the determined inflection points are linked to a field limit or a measuring bodily limit, as the case may be. In the example shown, the inflection point 29 can be linked to the bodily limit 1 of the measuring body 13, which is located in the negative X-direction, and the inflection point 30 can be linked to the bodily limit 2 of the measuring body 13, which is located in the positive X-direction. In the same manner, the bodily limits of the measuring body 13 in the Y-direction can be determined by means of a dose profile in the Y-direction. In FIG. 1, the bodily limits in the Y-direction are marked with the reference signs 16 and 17. The inflection point 3 can be linked to the field limit located in the negative X-direction and the inflection point 4 can be linked to the field limit located in the positive X-direction. In the same manner, a determination of the field limits in the Y-direction can be carried out on the basis of a dose profile in the Y-direction.

After determining the two bodily limits of the measuring body 13, the center position of the measuring body 13 can be determined through the arithmetic averaging of the two spatial coordinates of the boundary points. Preferably, the distances of the bodily limits in the X-direction and in the Y-direction are used to determine the center point position. In the same manner, the central beam position can be determined through the arithmetic averaging of the spatial coordinates of the boundary points after defining the two field limits 3 and 4. Preferably, the distances of the field limits in the X-direction and in the Y-direction are used to determine the central beam position.

In the further step g) of the method, the positions of the center point of the measuring body 13 and of the irradiation field relative to the EPID center are determined on the basis of the linked bodily limits of the measuring body 13 and the linked field limits of the irradiation field. Steps d) to g) are carried out for the directions X and Y. In step h), the difference vector in the EPID plane, which points from the center of the measuring body 13 to the central beam penetration point through the EPID plane, is projected into the isocenter plane in accordance with equation (1). Steps b) to h) are carried out for all prescribed support arm angles, collimator angles and couch angles (of the patient couch).

Finally, the vector components of the differential vector are used to correct the current radiological isocenter.

The method achieves a spatial resolution of 0.01 mm with a standard clinical EPID, which corresponds to a resolution 39.2 times better than the standard EPID.

The measurement conditions for the dose profile shown in FIG. 2 were determined as follows: support arm angle=0°, collimator angle=0°, couch angle=0°, nominal field size=15×15 mm$^2$, focus-EPID distance=1.5 m (magnification factor=1.5), photon energy=6 MeV and irradiated dose=12 MU. The dose D is measured by the EPID in the unit [CU] (calibrated dose unit), where 1 CU=1 Gy under calibration measurement conditions. The sizes ax and $CAX_X$ are the field width or central beam position, as the case may be, in the X direction. For the same irradiation field without a Winston-Lutz pointer, the same values were determined for such sizes. The graphic was created using MATLAB® (version R2007a).

FIG. 2b shows the definition of all four 50% dose points of the dose profile in the X-direction of FIG. 2a, which are required to determine the measuring bodily limits, irradiation field limits and the positions of the center point of the measuring body and the central beam. All 50% dose levels are defined as the arithmetic mean of a local dose minimum and a local dose maximum. The smallest of all local dose maxima is specified as a 100% dose. The smallest possible values for the measuring body and for the irradiation field are used as dose minima. If both the respective dose maximum and the respective dose minimum for calculating the 50% dose point are minimal, its dose value will also be minimal. Thereby, every 50% dose point is in the area of the inflection point there. Both aspects increase the resolution of the method. The fact that a low 50% dose point is advantageous can be physically explained as follows: The lower the 50% dose point of the field, the less interference is caused by the scattered photons generated in the measuring body, since the distance of the measuring body to the 50% dose point increases. And vice versa; the lower the 50% dose point of the measuring body, the less interference is caused by the scattered photons generated by the field limitation (block apertures, leaves of an MLC or a circular collimator), since the distance of the field limitation from the 50% dose point increases. FIG. 2b shows a dose profile for determining the geometric properties of the irradiation field and the measuring body in the X-direction. However, in the method, at least two different dose profiles are cut out of a dose image, which profiles have different Y-coordinates. In the Y-direction, the procedure is the same. This also contributes to the good resolution or error minimization, as the case may be, of the method. The equations of determination are as follows:

$$D_{100\%}=\min[D_{max}(-X),D_{max}(+X),D_{max}(-Y),D_{max}(+Y)],$$

$$D_{min}(\text{field})=0[CU],$$

$$D_{50\%}(MK)=[D_{100\%}+D_{min}(MK)]/2,$$

$$D_{50\%}(\text{field})=[D_{100\%}+D_{min}(\text{field})]/2=D_{100\%}/2,$$

$$\Delta X(MK)=[X_1(MK)+X_2(MK)]/2,$$

$$\Delta Y(MK)=[Y_1(MK)+Y_2(MK)]/2,$$

$$\Delta CAX_X=[X_1(\text{field})+X_2(\text{field})]/2,$$

$$\Delta CAX_Y=[Y_1(\text{field})+Y_2(\text{field})]/2,$$

$$\Delta X_{ISO}=\Delta CAX_X-\Delta X(MK),$$

$$\Delta Y_{ISO}=\Delta CAX_Y-\Delta Y(MK).$$

Legend for the Equations:

MK=measuring body or Winston-Lutz pointer or tungsten sphere (the Winston-Lutz pointer used for explanation in the exemplary embodiment of the method is a commercial pointer manufactured by BRAINLAB AG, Feldkirchen, Germany)

Field=irradiation field with specific field width (X direction) and field length (Y direction)

Coordinate system=EPID coordinate system $D_{100\%}$=100% substitute dose (compare 100% dose of the IEC 60976 standard)

$D_{50\%}$(field)=50% dose to determine the field width and field length by means of the inflectional tangent localized there $D_{50\%}$(MK)=50% substitute dose for determining the measuring bodily limits by means of the inflectional tangent localized there $D_{max}$(-X)=local dose maximum of the X-profile with a negative spatial coordinate $D_{max}$(+X)=local dose maximum of the X-profile with a positive spatial coordinate $D_{max}$(-Y)=local dose maximum of the Y-profile with a negative spatial coordinate $D_{max}$(+Y)=local dose maximum of the Y-profile with a positive spatial coordinate $D_{min}$(MK)=local dose minimum of both dose profiles in the area of the measuring body $D_{min}$(-X)=local dose minimum of the X-profile at the field edge with a negative spatial coordinate $D_{min}$(+X)=local dose minimum of the X-profile at the field edge with a positive spatial coordinate $D_{min}$(-Y)=local dose minimum of the Y-profile at the field edge with a negative spatial coordinate $D_{min}(+Y)$=local dose minimum of the Y-profile at the field edge with a positive spatial coordinate $D_{min}(field)$=uniform dose minimum of both dose profiles at all field edges $X_1(MK)$=limit of the measuring body in the negative X-direction $X_2(MK)$=limit of the measuring body in the positive X direction $Y_1(MK)$=limit of the measuring body in the negative Y-direction $Y_2(MK)$=limit of the measuring body in the positive Y-direction $X_1(field)$=position of the field limit in the negative X-direction $X_2(field)$=position of the field limit in the positive X direction $Y_1(field)$=position of the field limit in the negative Y-direction $Y_2(field)$=position of the field limit in the positive Y-direction $\Delta X(MK)$=position of the center point of the measuring body in the X-direction relative to the EPID center $\Delta Y(MK)$=position of the center point of the measuring body in the Y-direction relative to the EPID center $\Delta CAX_X$=position of the central beam of the irradiation field in the X-direction relative to the EPID center $\Delta CAX_Y$=position of the central beam of the irradiation field in the Y-direction relative to the EPID center $\Delta X_{ISO}$=central beam deviation relative to the center point of the measuring body in the X-direction (measured in the EPID plane)

$\Delta Y_{ISO}$=central beam deviation relative to the center point of the measuring body in the Y-direction (measured in the EPID plane)

Figure 3:
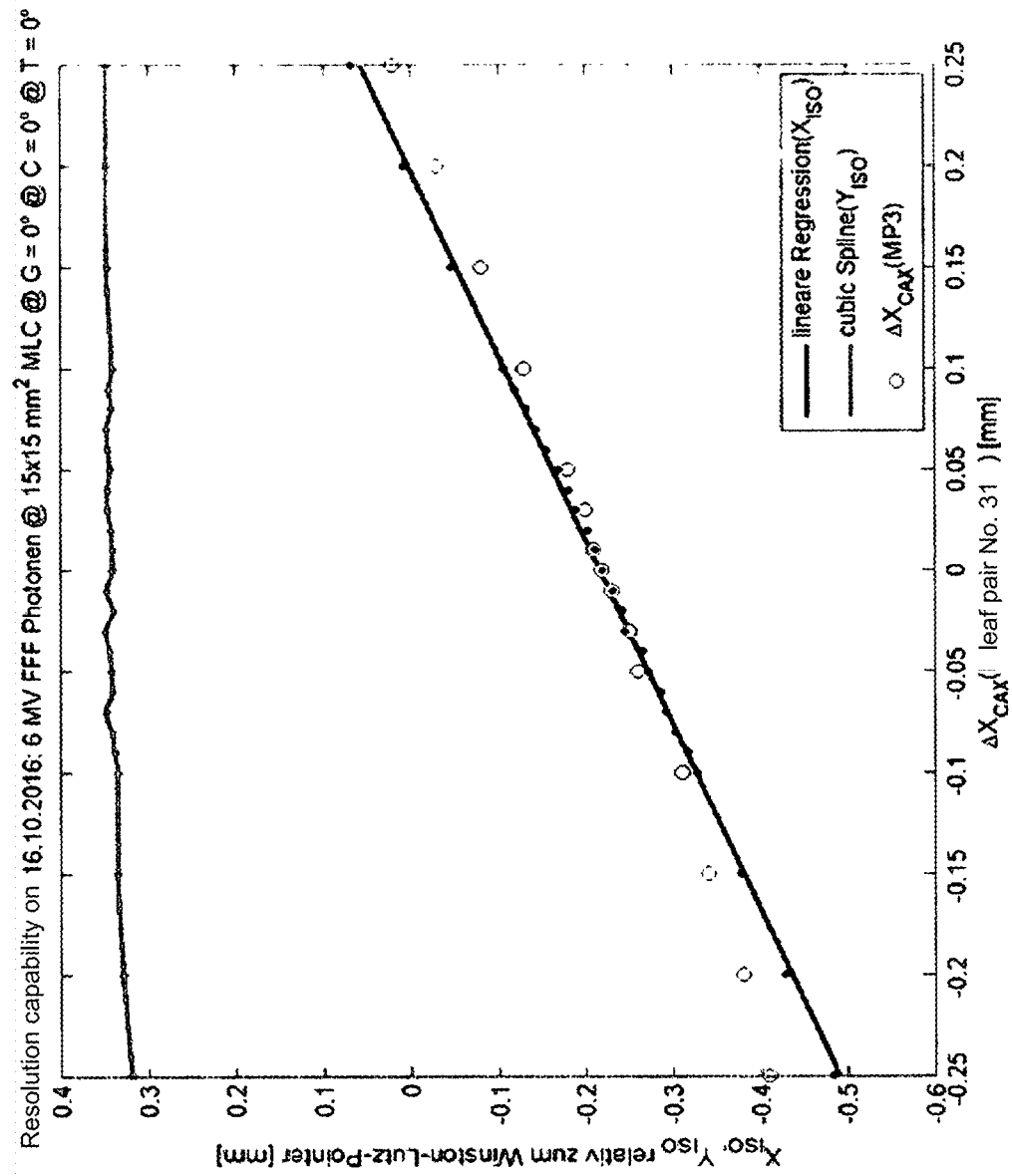

To prove the spatial resolution of 0.01 mm achievable by the method, the leaf positions of an MLC are varied with the smallest possible step size of 0.01 mm. Thereby, the determination of the respective central beam position is carried out in an MP3 large water phantom with a high-resolution dosimetry diode E type 60012 as a dose detector, a TANDEM two-channel electrometer and the MEPHYSTO® mc² software program made by PTW GmbH (Freiburg, Germany). In contrast to the method, in which the focus-EPID distance amounts to 150 cm, the focus-detector distance for the detection of the spatial resolution is 100 cm. When carrying out the verification of the spatial resolution, a photon energy=6 MeV, a dose rate=400 MU/min, a dose integration time per measuring point=1 s and a detector step size=0.2 mm to 1 mm are set. FIG. 3 shows the verification of the spatial resolution. The radiological determination of the central beam deviations $\Delta X_{CAX}$ or $\Delta Y_{CAX}$, as the case may be, from the theoretical isocenter of a radiation therapy device in the large water phantom represents the gold standard in radiation therapy. The black dots mark the central beam displacements between a centrally located pair of leaves (here, no. 31) in the X-direction, as determined by the Winston-Lutz method. For this purpose, the pairs of leaves limiting the irradiation field were shifted in a defined manner; the smallest adjustable step size for the "High-Definition 120" MLC used amounts to 0.01 mm. The associated regression line has the equation $X_{ISO}=1.094 \cdot \Delta X_{CAX}-0.217$ mm. The correlation coefficient according to Pearson amounts to r=0.9991 at p=0.0000 (probability of non-correlation) and thus indicates an almost ideal linear relationship. The measurement results in the large water phantom MP3 are shown as black circles. With both measuring methods, the smallest leaf displacement±0.01 mm can be resolved. The slightly increasing plot of the central beam deviation $Y_{ISO}$ during the Winston-Lutz test, which lasted 15 min in this case, proves the relaxation of the support arm at 0° as a result of a positive bending moment around the spatially fixed X-axis acting on the support arm and radiator head. At $|\Delta X_{CAX}| \geq 0.05$ mm, the black dots of the Winston-Lutz analysis no longer correspond to the black circles of the MP3 measurement, since, in the first case, the medium at the field edge and in the field is not homogeneous: air, plastic and tungsten versus homogeneous water. The graphic in FIG. 3 was generated using MATLAB® (version R2007a).

Figure 4:
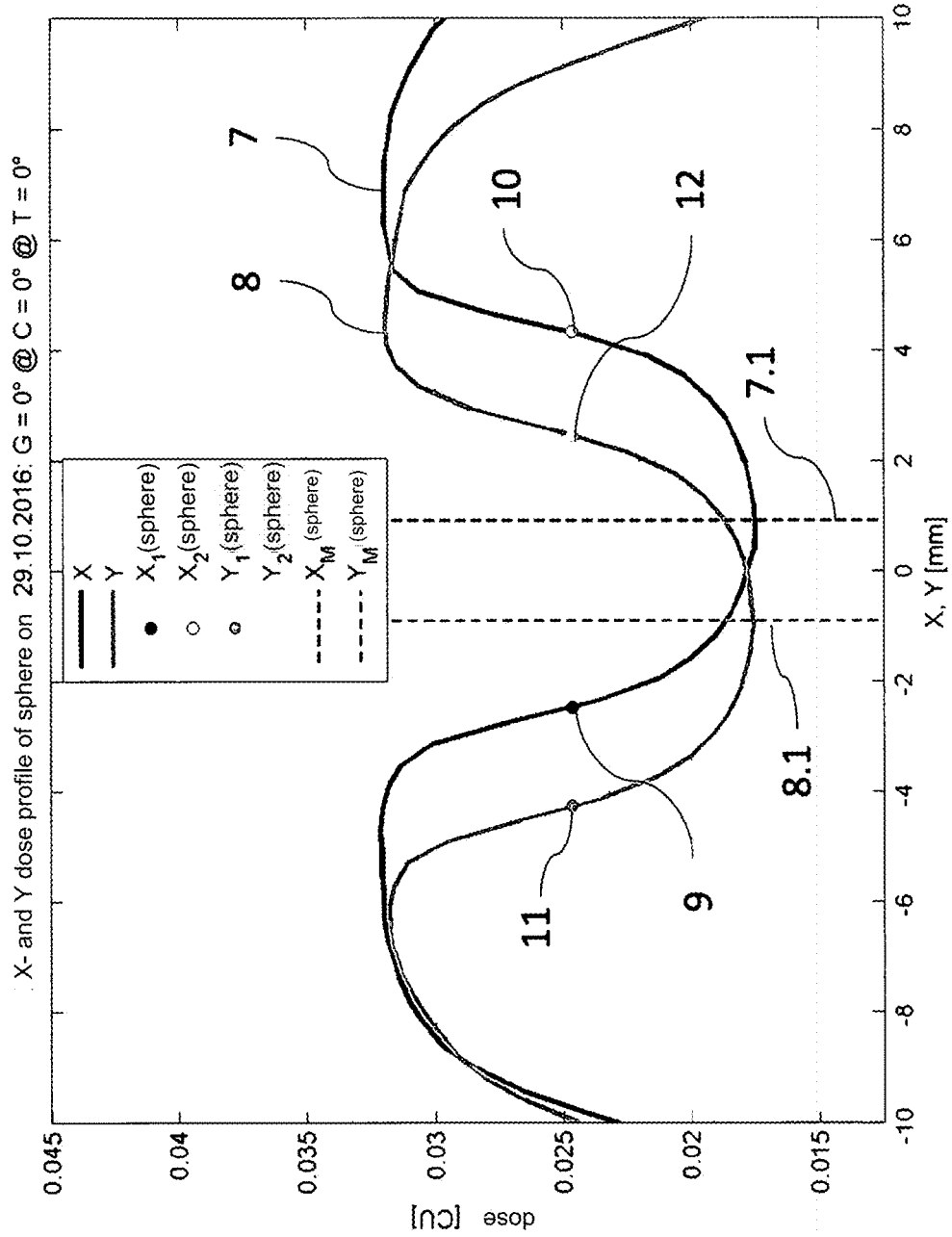

FIG. 4 shows dose profiles of the Winston-Lutz pointer as the measuring body in the X-direction 7 and Y-direction 8 with the inflection points for defining the measuring bodily limits in the X-direction 9 and 10 and in the Y-direction 11 and 12. The dotted vertical lines 7.1 and 8.1 indicate the position of the sphere center point in the X-direction (7.1) and in the Y-direction (8.1). The stretch factor amounts to $k^{-1}>1$ with the definition in equation (1). The graphic in FIG. 4 was created by means of MATLAB® (version R2007a).

Figure 5:
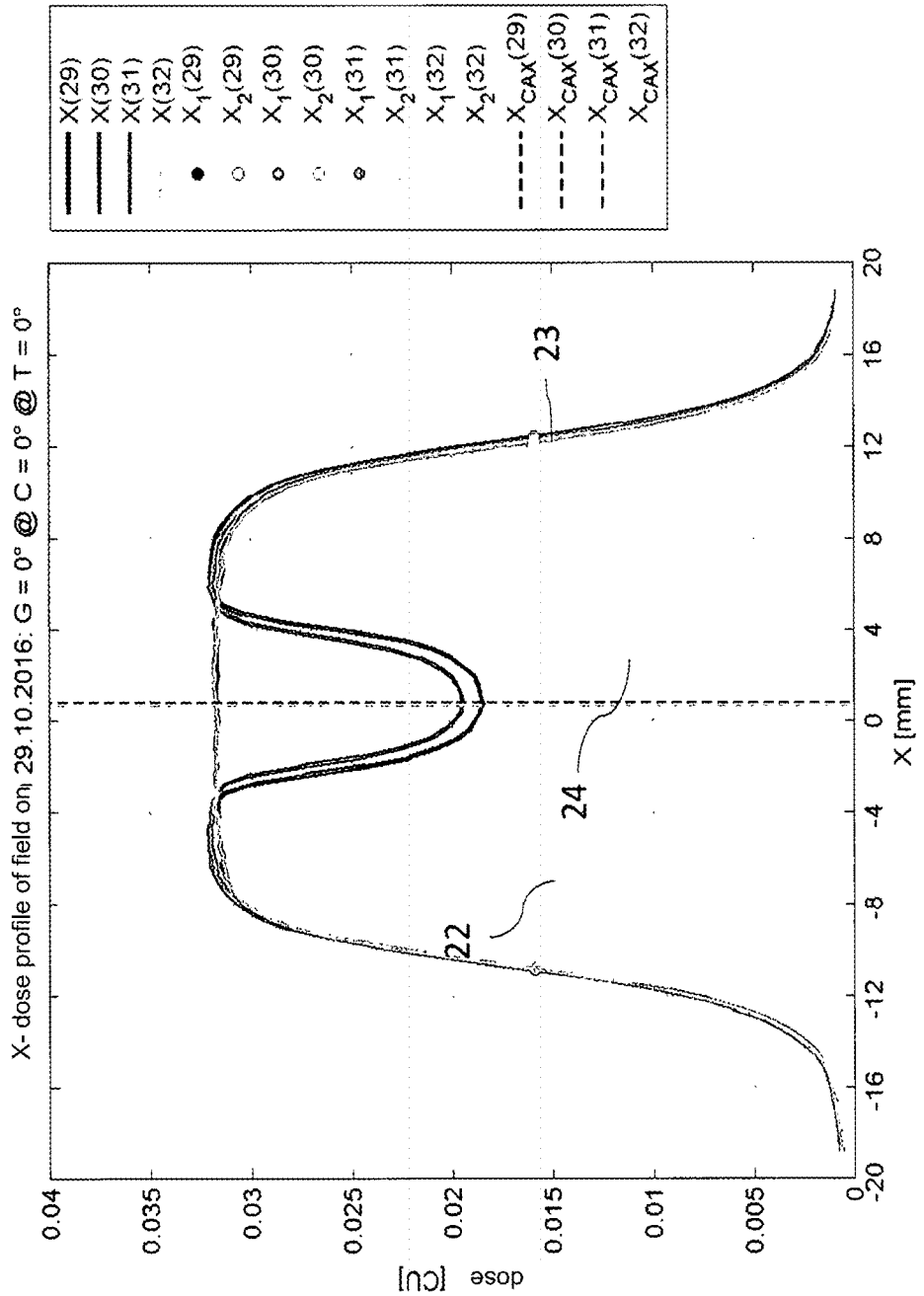

FIG. 5 shows four dose profiles of an MLC-limited irradiation field of the size 15×15 mm² in the X-direction under the leaf pairs no. 29 to no. 32, with the inflection points 22 and 23, for defining the field limits of the irradiation field and with the positions of the local central beams (dashed vertical lines 24). The stretch factor amounts to $k^{-1}>1$ with the definition in equation (1). The graphic in FIG. 5 was created by means of MATLAB® (version R2007a).

Figure 6:
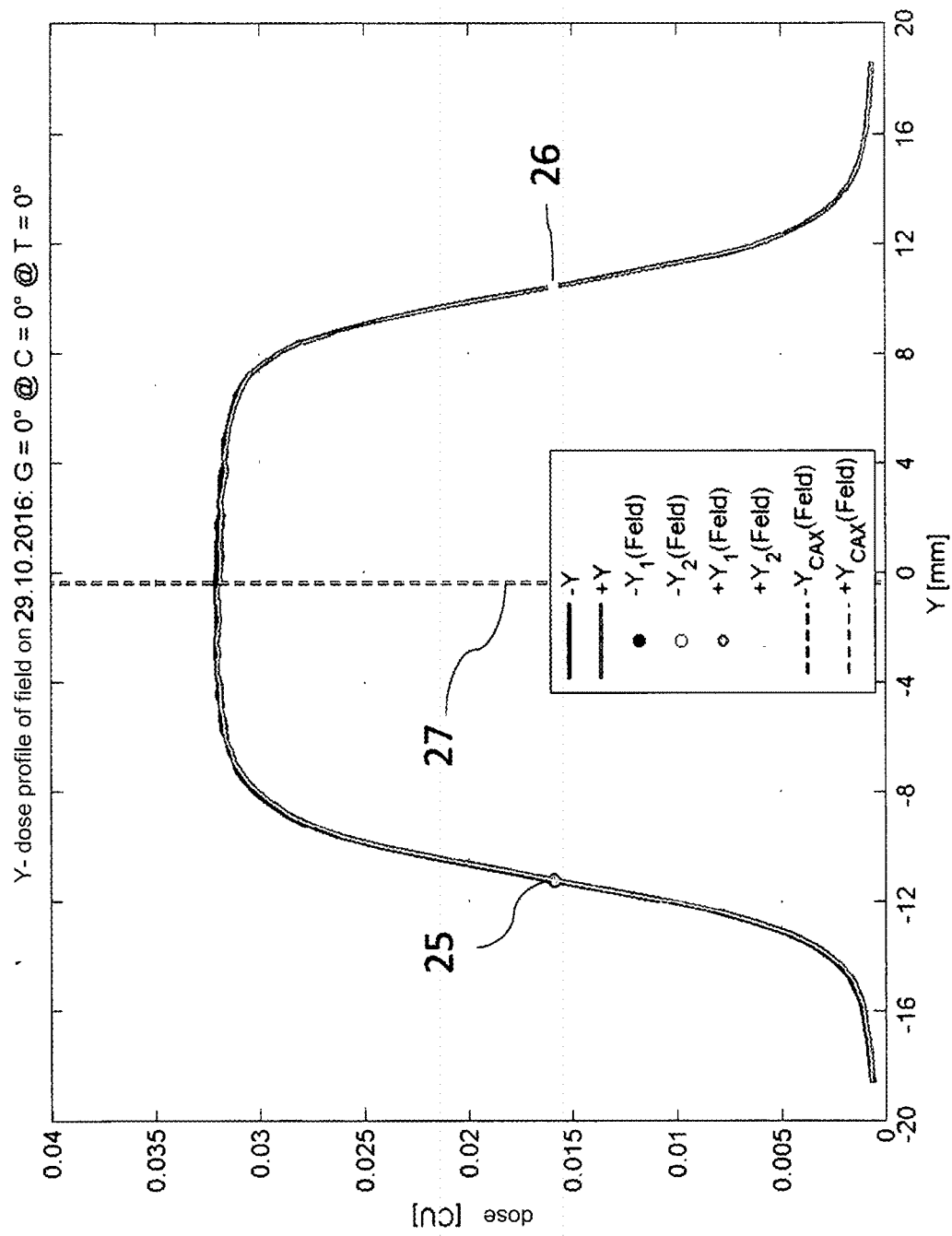

FIG. 6 shows an additional two dose profiles of an MLC-limited irradiation field of the size 15×15 mm² in the Y-direction between the closed leaf pairs no. 27 and no. 34, with the inflection points 25 and 26, for defining the field limits and the positions of the local central beams in the Y-direction (dashed vertical lines 27). The stretch factor amounts to $k^{-1}>1$ with the definition in equation (1). The graphic in FIG. 6 was created by means of MATLAB® (version R2007a).

Figure 7:
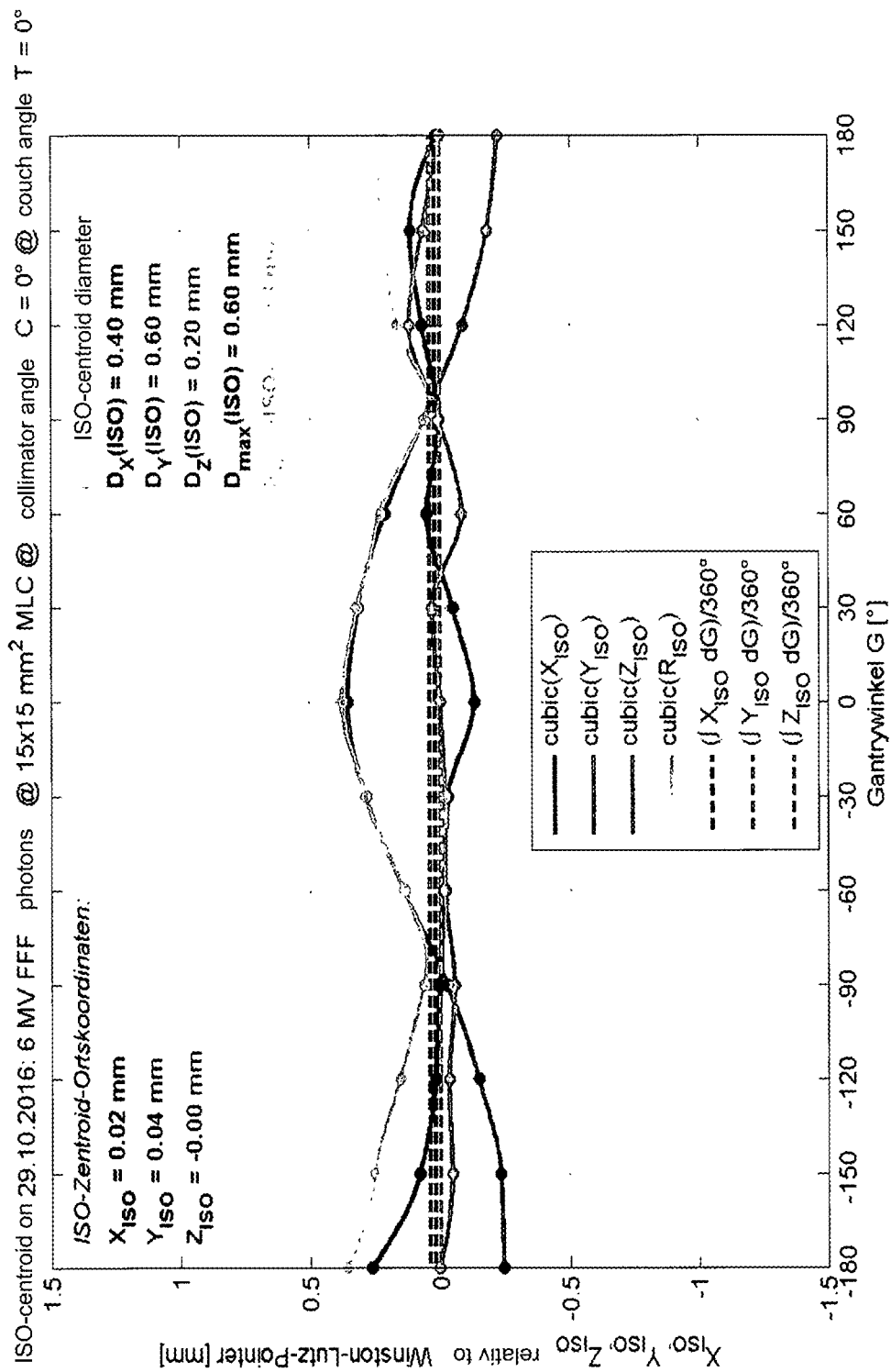

FIG. 7 shows a schematic diagram of the geometry of an isocentroid dependent on the support arm angle of a Novalis radiation therapy device powered by TrueBeam™ STx (VARIAN Medical Systems, Inc., Palo Alto, Calif., U.S. and BRAINLAB AG, Feldkirchen, Germany). The solid lines in the colors of black, dark gray and gray represent the central beam deviations relative to the measuring body in the directions X, Y or Z, as the case may be, of the spatially fixed coordinate system. The dashed lines mark the spatial coordinates of the isocentroid in such directions. The diameters in the axes of the inertial system, their maximum and the spatial coordinates are also output as numerical values. In addition, the amount of the spatial radius vector as a function of the support arm angle is shown (light gray line) and its maximum is indicated. Analog result representations are generated by means of MATLAB® (version R2007a) for the solitary isocentroids dependent on the collimator and couch angle along with the global isocentroid, which combines all three solitary isocentroids.

Figure 8:
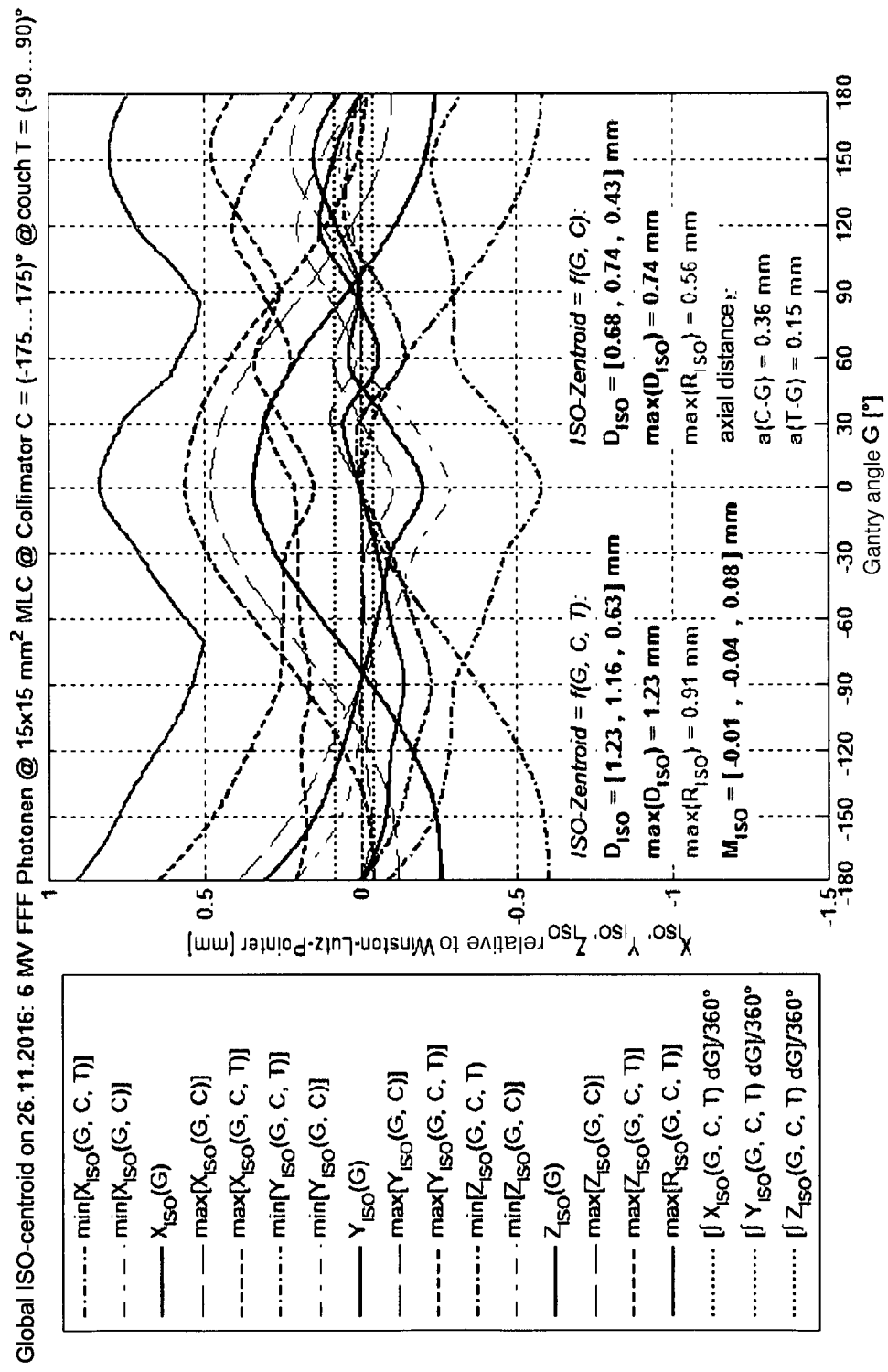

FIG. 8 shows a graphical representation of the geometry of the global isocentroid of a Novalis medical electron linear accelerator powered by TrueBeam™ STx using MATLAB®. The solid lines in the colors of black, dark gray and gray represent the central ray deviations dependent on the support arm angle relative to the Winston-Lutz pointer in the directions X, Y or Z, as the case may be, of the inertial system. The limits of the additional negative and positive scattering bands for the superimposed collimator rotation are shown as thin dash-point lines or dashed lines, as the case may be. If the central beam deviations dependent on the couch angle are added, the corresponding lines are shown as thick lines. The light gray line shows the plot dependent on the support arm angle of the maximum radius of the global isocentroid. The point lines mark the spatial coordinates of the global isocentroid. The diameters in the axes of the inertial system, their maxima and the spatial coordinates are also output as numerical values. In addition, the diagram below right shows the spatial distances of the rotation axes of the collimator and the couch relative to the support arm rotation axis.

The invention claimed is:

1. A method for EPID-based verification, correction and minimization of an isocenter of a radiotherapy device, the radiotherapy device having
    at least one patient couch rotatable about a couch axis,
    a support arm rotatable about a support arm axis,
    a radiator head arranged on the support arm for generating a therapy beam,
    a rotatable collimator,
    a projection device for projecting a radiological isocenter at a projection position and
    a digital recording system (EPID) for acquiring dose images by the therapy beam,
    wherein the following steps are performed:
    a) a measurement body is positioned, by the projection device, at a projection position in a current radiological isocenter of the radiotherapy device,
    b) an irradiation field, limited by the collimator, is applied for at least one predefined angular setting of the support arm, the patient couch and the collimator and thereby
    c) at least one common dose image of the measurement body and the irradiation field is captured using the EPID,
    d) a dose profile for each direction within an EPID coordinate system is created on the basis of the common dose image and
    e) in a plot of the dose profile, an inflection point between a local dose minimum and a local dose maximum, and between a local dose maximum and a local dose minimum is determined at each of both expected bodily limits of the measuring body in an X-direction of the EPID coordinate system and at each of both expected bodily limits of the measuring body in a Y-direction of the EPID coordinate system, and
    f) positions of the inflection points determined in step e) are linked to the bodily limits of the measurement body in the X-direction and in the Y-direction,
    g) a position of a center point of the measurement body relative to an EPID-center is determined in the dose image on the basis of the bodily limits of the measurement body, the steps d) to g) being carried out in the same way for field limits and a field center point of the irradiation field, and
    h) a differential vector is determined from a deviation in the position of the center point of the measurement body from the EPID-center and from a deviation in position of the field center point of the irradiation field from the EPID-center, and
    i) vector components of the differential vector are used to correct the current radiological isocenter,
    wherein the irradiation field is applied taking into account minimum values of a field size, a relaxation time of the support arm, a dose per irradiation field, and/or a focus-EPID distance.

2. The method according to claim 1, wherein the method steps b) to h) are carried out with an increment of a maximum of 30° of angular freedoms of the patient couch, the support arm and the collimator.

3. The method according to claim 1, wherein differential vectors, which can be determined from the dose images taken from different angular positions of the patient couch, the support arm and the collimator, are used to determine a size and position of spatial isocenters, wherein vector components of associated position vectors of the spatial isocenters are used to correct the radiological isocenter.

4. The method according to claim 3, wherein the associated position vectors of the spatial isocenters are used for calibrating a patient positioning system.

5. The method according to claim 3, wherein the associated position vectors of the spatial isocenters are used to correct the projection device.

6. The method according to claim 3, wherein all device-specific parameters of the radiotherapy device influencing the spatial isocenters are optimized by minimizing a predetermined target function.

7. The method according to claim 3,
    wherein the radiotherapy device is a therapy simulator, and
    wherein the spatial isocenters are determined, corrected and minimized.

8. The method according to claim 1, wherein the inflection point(s) is/are determined in a range of a 50% dose point between a dose minimum and a dose maximum of the dose profile and/or in a range of a 50% dose point between a dose maximum and a dose minimum of the dose profile.

9. The method according to claim 8, wherein the inflection point(s) in the range of the 50% dose point is/are defined between two pixels, of which a first pixel represents a dose less than 50% and a second pixel adjacent to the first pixel represents a dose greater than 50%.

10. The method according to claim 1, wherein, when using a multi-leaf collimator (MLC), steps d) to h) are carried out for each pair of leaves of the MLC limiting the irradiation field.

11. The method according to claim 1, wherein a support arm angle of ≠0° is set when a patient couch angle is varied.

12. The method according to claim 1, wherein a global spatial isocenter of the radiotherapy device is determined from individual central beam deviations in three spatial directions X, Y and Z of three spatial isocenters of the support arm, the collimator and the patient couch.

13. The method according to claim 1, wherein the method steps d) to i) are carried out automatically under control of a software program.

14. The method according to claim 1, wherein an isocenter of the patient couch is alternatively determined at a support arm angle=0° by means of a radiological patient positioning system independent of the radiotherapy device.

* * * * *